Oct. 3, 1933. C. SALBACH Plant Pat. 77
GLADIOLUS
Filed April 24, 1933
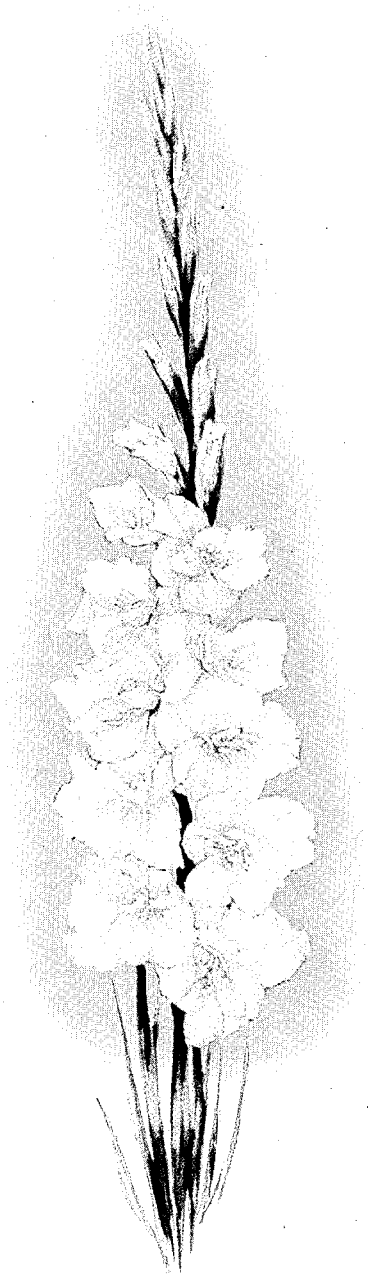
INVENTOR
Carl Salbach
By Orville M. Kile
Plant Patent Agent Patented Oct. 3, 1933

Plant Pat. 77

UNITED STATES PATENT OFFICE

Plant Pat. 77

GLADIOLUS

Carl Salbach, Berkeley, Calif.

Application April 24, 1933. Serial No. 667,702

1 Claim. (Cl. 47—60)

My present invention relates to improvements in gladioli of the yellow or golden color and of the type notable for size and quantity of bloom. The object of this invention is to provide a gladiolus of superior yellow or golden coloring combined with exceptionally large spikes of flowers bearing a large number of large-sized and exceptionally well-shaped and well-placed florets, as well as possessing superior keeping qualities when cut. This combination gives a gladiolus long desired by florists and fanciers.

My new variety of gladiolus originated as a seedling produced from cross pollination work carried on by myself. To the best of my knowledge and belief the parents of this new variety were the variety "Golden Dream" and an unnamed yellow variety produced by myself. It first bloomed in August 1931.

The accompanying illustration shows as nearly as the artist could paint it, a flowering spike as it would normally appear when fresh cut, also some of the leaves. The painting does not, however, convey the full beauty of the flower as viewed in nature where the great size is appreciated and each floret stands out clearly yet displays a softness of coloring impossible to depict with paints on paper.

The plant is a vigorous grower and the tips of the spikes usually reach a height of 40 to 50 inches above the ground. Foliage is moderate in quantity and light green in color.

Reproduction is very rapid because of the large number of cormels or cormlets produced.

The spikes are taller than those of somewhat similar yellow or golden varieties grown under the same conditions of soil and climate. The spikes ordinarily have 22 to 24 buds and 10 to 12 of these will be opened at one time. Yellow or golden varieties somewhat similar to this new variety, such as "Souvenir" and "Golden Dream" fall far short of the number of buds and florets displayed by this new variety; "Souvenir" having ordinarily 10 to 12 buds with not more than 4 or 5 open at any one time, and "Golden Dream" having sometimes as many as 18 buds with only 4 or 5 open at one time.

The perfect spacing and symmetrical arrangement of the buds and florets on the flower spike of my new variety are particularly notable. The florets all face the same way and stand close against one another so that there are no objectionable open spaces to detract from the beauty of the flowering spike.

There is also pleasing proportion of size as between stem and flower spike so that even with as many as twelve florets open at once, enough unopened buds remain to give the flower excellent balance.

The florets are each considerably larger than those of either "Souvenir" or "Golden Dream" in addition to occurring so many more to the spike. A typical floret at the bottom of the spike will measure 4 inches across.

The form of each floret is more nearly perfect than in the somewhat similar varieties above mentioned.

The color most nearly approaches "amber yellow," according to Ridgway's Color Standards and Nomenclature, edition of 1912, Plate XVI, although it is also very close to "Empire yellow," Plate IV. This is a deeper tone than is shown by either the "Souvenir" or "Golden Dream" varieties above mentioned. The coloring of my new variety while clear and deep is at the same time soft and gives an effect which the artist is unable to reproduce. The florets have no blotches, spots or markings of any color other than the deep yellow as described. This color is surprisingly uniform in all parts of the florets, showing practically no variation at all.

Another notable characteristic of this new variety that makes it particularly valuable to the florist, is found in the fact that all the buds bloom out well when the spike is cut and placed in water. Even the topmost bud will develop fully under these circumstances. This is a characteristic not possessed by the variety "Golden Dream."

The substance of the florets is substantial and gives them excellent keeping and shipping qualities.

The most notable characteristics which readily distinguish my new variety of gladiolus from all other yellow or golden varieties and particularly from the varieties known as "Souvenir" and "Golden Dream" are:

First, the exceptionally large number of buds that occur on a single flower spike.

Second, the exceptionally large number of florets that open at one time.

Third, the unusual perfection of form of each individual floret.

Fourth, the symmetry and desirability of arrangement and location of the florets on the stem.

Fifth, the deep, clear yet soft "amber yellow" to "Empire yellow" coloring of the florets, and the lack of any variation in coloring in the various portions of the floret.

Sixth, the substantial substance of the florets combined with their characteristic of opening up well in water, giving valuable keeping qualities for the florist.

Seventh, the rapid reproductive qualities.

Having thus disclosed my invention, I claim:

The variety of gladiolus plant herein described and illustrated, characterized particularly by the large number of large sized buds and florets produced on each flower spike and the large number open at one time, by the unusual perfection of form and arrangement of these florets which have exceptional keeping and show qualities, and by the deep, clear yet soft "amber yellow" to "Empire yellow" color of said florets; also by variety's superior reproductive qualities.

CARL SALBACH.